US007615358B2

(12) United States Patent
Pachmann et al.

(10) Patent No.: US 7,615,358 B2
(45) Date of Patent: Nov. 10, 2009

(54) METHOD FOR DETERMINING THE CONCENTRATION OF VITAL EPITHELIAL TUMOR CELLS IN A BODY FLUID

(76) Inventors: Ulrich Pachmann, Brandenburger Str. 30, 95448 Bayreuth (DE); Katharina Pachmann, Brandenburger Str. 30, 95448 Bayreuth (DE)

( * ) Notice: Subject to any disclaimer, the term of this patent is extended or adjusted under 35 U.S.C. 154(b) by 89 days.

(21) Appl. No.: 11/733,259

(22) Filed: Apr. 10, 2007

(65) Prior Publication Data

US 2007/0248999 A1    Oct. 25, 2007

Related U.S. Application Data

(60) Provisional application No. 60/793,462, filed on Apr. 20, 2006.

(51) Int. Cl.
G01N 33/48 (2006.01)
G01N 33/53 (2006.01)
G01N 33/547 (2006.01)

(52) U.S. Cl. .......................... 435/7.2; 436/63; 436/64; 436/813

(58) Field of Classification Search ....................... None
See application file for complete search history.

(56) References Cited

U.S. PATENT DOCUMENTS

| 5,751,839 | A | 5/1998 | Drocourt et al. | |
|---|---|---|---|---|
| 6,107,462 | A * | 8/2000 | Rine et al. | 530/350 |
| 6,365,362 | B1 | 4/2002 | Terstappen et al. | |
| 7,056,657 | B2 * | 6/2006 | Terstappen et al. | 435/5 |
| 2002/0168657 | A1 * | 11/2002 | Chen et al. | 435/6 |

FOREIGN PATENT DOCUMENTS

| EP | 1 262 776 | 5/2002 |
|---|---|---|
| WO | WO 99/41613 | 8/1999 |

OTHER PUBLICATIONS

Shen et al, PNAS, 1984, vol. 81, pp. 1445-1447.*
Kranz (The Lancet, 2000, vol. 356, pp. 1242-1243).*
Kranz et al (Blood, 1989, vol. 73, pp. 1942-1950).*
Carlson, "Finding & Identifying Disseminated Tumor Cells as Biomarkers for Solid Cancers," *Oncology Times*, 2005, 27(11):10-11.
Clement et al., "Differential interaction of magnetic nanoparticles with tumor cells and peripheral blood cells," *J. Cancer Res. Clin. Oncol.*, 2006, 132:287-292.
Hümmer et al., "Adjuvante homöopathische Therapie bei konventionell behandeltem Mammakarzinom," *AHZ*, 2005, 250:127-133 (includes English summary).
Jungwirth-Schill et al., "Antibodies against carbohydrate targets on GPIB/V/IX complex in thrombocytopenic patients as detected by MAIPA," *Vox Sanguinis*, 2000, 78(suppl 1), Poster 063.
Pachmann and Pachmann, "Laser Scanning Cytometry and Magnetic Bead Enrichment for Rapid Quantitative Enumeration of Minimal Numbers of Tumor Cells in Peripheral Blood and Bone Marrow in Breast Cancer Patients," *Thirty-Sixth Annual Meeting of the American Society of Clinical Oncology*, May 20-23, 2000, New Orleans, LA, 19:138a, Abstract 541.
Pachmann and Pachmann, "The MAINTRAC Approach for Detection of Circulating Tumour Cells: Sensitivity, Specificity, Reproducibility," *Vox Sanguinis*, 2000, 78(suppl 1), Poster 615.
Pachmann and Pachmann, "Minimale residuale Tumorerkrankung bei soliden epithelialen Tumoren. Leserbrief: Neues automatisiertes Analyseverfahren," *Deutsches Ärzteblatt*, 2000, 23(S7):2630-2631 (includes English summary).
Pachmann et al., "Expression of bcr-abl mRNA in individual chronic myelogenous leukaemia cells as determined by in situ amplification," *Br. J. Haematol.*, 2001, 112:749-759.
Pachmann et al., "Laser Scanning Cytometry and magnetic bead enrichment for unequivocal detection of aberrant cells in peripheral blood," *Laborwelt*, 2001, 4:23-26 (includes English summary).
Pachmann et al., "Monitoring the efficacy of adjuvant therapy in breast cancer by quantifying circulating tumor cells using the MAINTRAC analysis (laser scanning cytometry of magnetic bead enriched cells)," *Analytical Cellular Pathology*, 2001, 22:59, Abstract P006.
Pachmann, "Nachweis minimaler zirkulierender Tumorzellen mit Hilfe mikroflourimetrischer Analysen am Laser Scanning Cytometer (LSC)," *Innovationsforum*, 2001, 18-19.
Pachmann et al., "An approach to standardize the detection circulating tumor cells comparing different methods for analysis in peripheral blood and bone marrow," *Onkologie*, 2003, 26(S5):191, Abstract P932.
Pachmann et al., "Influence of primary tumor chemotherapy in breast cancer on circulating tumor cells. Indications for massive cell release into circulation concurrent with tumor size reduction," *Breast Cancer Research and Treatment*, 2004, 88:S224, Abstract 6014.
Pachmann and Camara, "Influence of Neoadjuvant Therapy in Breast Cancer on Circulating Tumor Cells," 95th *Annual Meeting of the American Association for Cancer Research*, 2004, p. 94, Abstract LB-161.
Pachmann, "Neoadjuvant Chemotherapy for Breast Cancer Can Cause Release of Tumor Cells," *Oncology News International*, 2005, 3:29.
Pachmann et al., "Quantitative monitoring of circulating epithelial cells for individual therapy control in lung and breast cancer during neoadjuvant treatment, surgery and adjuvant chemotherapy," *J. Clin. Oncol.*, 2005, 23:36s, Abstract 631.

(Continued)

*Primary Examiner*—Karen A Canella
(74) *Attorney, Agent, or Firm*—Fish & Richardson P.C.

(57) ABSTRACT

A method for determining the concentration of vital epithelial tumor cells in a body fluid is disclosed. The method comprises obtaining from the body fluid of a test subject a test specimen, labeling the epithelial tumor cells contained in said test specimen, applying the test specimen to a support, where the epithelial tumor cells adhere and identifying vital cells of the adhering epithelial tumor cells by means of their morphology. The method does not comprise an enrichment of epithelial tumor cells by means of binding to paramagnetic or magnetic particles and applying a magnetic force to the particles.

15 Claims, 1 Drawing Sheet

OTHER PUBLICATIONS

Pachmann et al., "Standardized quantification of circulating peripheral tumor cells from lung and breast cancer," *Clin. Chem. Lab. Med.*, 2005, 43(6):617-627.

Pachmann, "Longtime Recirculating Tumor Cells in Breast Cancer Patients," *Clin. Cancer Res.*, 2005, 11(15):5657-5658.

Pachmann et al., "Quantification of the response of circulating epithelial cells to neoadjuvant treatment foe breast cancer: a new tool for therapy monitoring," *Breast Cancer Res.*, 2005, 7:R975-R979.

Pachmann et al., "Circulating tumor cells: Tools for monitoring and targets for therapy," *J. Clin. Oncol.*, 2006, 24:32s, Abstract 617.

Pachmann et al., "Detection and Quantification of Small Numbers of Circulating Tumour Cells in Peripheral Blood Using Laser Scanning Cytometer (LSC®)," *Clin. Chem. Lab. Med.*, 2001, 39(9):811-817.

Rolle et al., "Increase in number of circulating disseminated epithelial cells after surgery for non-small cell lung cancer monitoring by MAINTRAC® is a predictor for relapse: A preliminary report," *World Journal of Surgical Oncology*, 2005, 3:18-26.

Schwalbe et al., "Human plasma increases the magnetic separation of tumor cells from peripheral blood leukocytes," *5th Colloquium DFG-Priority Program Kolloidale magnetische Flüssigkeiten: Grundlagen Entwicklung und Anwendungen neuartiger Ferrofluide* 2004, 1 page.

Schwalbe et al., "Human Plasma Facilitates Enrichment of Circulating Epithelial Cells from Peripheral Blood," *Onkologie*, 2004, 27(S3):142, p. 630.

Schwalbe et al., "Selective reduction of the interaction of magnetic nanoparticles with leukocytes and tumor cells by human plasma," *J. Magnetism Magnetic Materials*, 2005, 293:433-437.

Schwalbe et al., "The Carboxymethyl Dextran Shell is an Important Modulator of Magnetic Nanoparticle Uptake in Human Cells," *Z. Phys. Chem.*, 2006, 220:125-131.

Schwalbe et al., "Improvement of the separation of tumour cells from peripheral blood cells using magnetic nanoparticles," *J. Phys.: Condens. Matter*, 2006, 18:S2865-S2876.

Tilz et al., "LSC—Laser scanning cytometry as an application for the detection of tumor cells in the peripheral blood. An experimental study," *Onkologie*, 2000, 23(57):Abstract 215.

Wagner et al., "Synthesis of oligonucleotide-functionalized magnetic nanoparticles and study on their in vitro cell uptake," *Appl. Organometal. Chem.*, 2004, 18:514-519.

Fang et al., "Detection of Rare MCF-7 Breast Carcinoma Cells From Mixtures of Human Peripheral Leukocytes by Magnetic Deposition Analysis," *Cytometry*, 1999, 36:294-302.

'HEA-FITC— Fluorescent Staining of Human Cells' [online], MACS, printed from the internet URL:www.miltenyibiotec.com, on Oct. 21, 2003, 2 pages.

Martin et al., "Immunomagnetic enrichment of disseminated epithelial tumor cells from peripheral blood by MACS," *Exp. Hematol.*, 1998, 26:252-264.

Pachmann et al., "Real Time Monitoring of the Efficacy of Adjuvant Therapy in Breast Cancer Quantifying the Reduction of Circulating Tumor Cells by MAINTRAC (Laser Scanning Cytometry of Magnetic Bead Enriched Cells)," *Breast Cancer Research and Treatment*, 2000, vol. 64, Abstract.

Pachman et al., "Detection and Quantification of Small Numbers of Circulating Tumour Cells in Peripheral Blood Using Laser Scanning Cytometer (LSC®)," *Clin. Chem. Lab Med.*, 2001, 39(9):811-817.

Rinas et al., "Detection of Breast Cancer Cells in Bone Marrow and Peripheral Blood with Magnetic Bead Enrichment and Laser Scanning Cytometry (MAINTRAC)," *Breast Cancer Research and Treatment*, 2000, vol. 64, Abstract.

Simon et al., "Epithelial glycoprotein is a member of a family of epithelial cell surface antigens homologous to nidogen, a matrix adhesion protein," *Proc. Natl. Acad. Sci. USA*, 1990, 87:2755-2759.

* cited by examiner

METHOD FOR DETERMINING THE CONCENTRATION OF VITAL EPITHELIAL TUMOR CELLS IN A BODY FLUID

CROSS-REFERENCE TO RELATED APPLICATIONS

This application claims priority under 35 U.S.C. §119(e) of U.S. Application No. 60/793,462, filed Apr. 20, 2006.

FIELD OF THE INVENTION

The invention relates generally to the determination of the concentration of vital epithelial tumor cells in a body fluid of a test subject suspected of having an epithelial tumor.

BACKGROUND

The invention relates generally to the field of the indication of solid tumors. It is well known that metastasis of solid tumors is the main reason for the high mortality rate from cancer. It is caused by cells which are disseminated in the lymph nodes and/or circulate in the peripheral blood. Some of the circulating tumor cells can, under certain circumstances, reach remote compartments where they begin to grow again. In the case of a number of tumors, these compartments are known. In breast cancer and cancer of the colon, one such compartment is the bone marrow. The incidence of the tumor cells in relation to normal bone marrow cells is at most $10^{-3}$ to $10^{-7}$ tumor cells/normal bone marrow cells. To obtain samples for bone marrow diagnosis, a special procedure is required in combination with or following an operation. Regular monitoring would require repetition of this procedure. Given the inconvenience this causes to the patient and the expenditure in terms of cost and time, it is sought to keep the number of surgical procedures as low as possible.

A further possibility is to examine the peripheral blood, which is much easier to access. However, the problem in this case is that detectable tumor cells in the peripheral blood are present only in extremely small numbers. Another difficulty is that the tumor cells circulating in the peripheral blood can contaminate the transplant in high-dose chemotherapy or autologous peripheral blood stem cell transplantation. Systems with a high level of sensitivity are therefore required to detect such a small number of residual tumor cells.

From U.S. Pat. No. 6,365,362 B1 a highly sensitive assay is known which combines immunomagnetic enrichment with multiparameter flow cytometric and immunocytochemical analysis to detect, enumerate and characterize carcinoma cells in the blood.

From EP 1 262 776 A2 a method for quantitative detection of vital epithelial tumor cells in a body fluid is known. This method comprises obtaining a defined quantity of a body fluid, labeling the vital epithelial tumor cells by addition of an antihuman epithelial antibody bound to magnetic particles, labeling the vital epithelial tumor cells by addition of antihuman epithelial antibodies bound to a fluorochrome, magnetically enriching the vital epithelial tumor cells, immobilizing the suspension so obtained on a support material, recording the vital epithelial tumor cells by means of laser scanning cytometry, and calculating the number of the cells in relation to the quantity of body fluid initially obtained.

SUMMARY

The invention is based on the discovery that a lot of vital epithelial tumor cells may be lost or damaged during magnetic enrichment and that the number of cells lost or damaged during magnetic enrichment varies strongly. The inventors further discovered that without the loss or damage of tumor cells due to magnetic enrichment the number of tumor cells in a specimen of a body fluid, e.g. peripheral blood, of an individual having an epithelial tumor is sufficient to be detected directly. The variation of the number of vital epithelial tumor cells detected from a specimen of a body fluid is much smaller if no enrichment procedure is performed.

The invention provides a method for determining the concentration of vital epithelial tumor cells in a body fluid comprising the following steps:

a) obtaining from the body fluid of a test subject a test specimen comprising a mixed cell population suspected of containing epithelial tumor cells, b) labeling the epithelial tumor cells by addition, to the test specimen or to a preparation obtained from the test specimen, of first antibodies or fragments of first antibodies that specifically bind to epithelial cells, which first antibodies or fragments of first antibodies are bound to a fluorochrome, c) applying the test specimen to a first support and incubating the test specimen on said first support to let the epithelial tumor cells in said test specimen adhere to said first support, and d) identifying and quantitating vital cells of the adhering epithelial tumor cells by means of their morphology and calculating the concentration of vital epithelial tumor cells in the body fluid, wherein no enrichment of the epithelial tumor cells by means of binding to paramagnetic or magnetic particles and applying a magnetic force to the particles is performed.

Normally cells from epithelial tissues are not found in the circulation, but are present in patients with malignant epithelial tumors, the most frequent of which are lung, breast and colon carcinoma. Therefore, the method according to the invention may be used to monitor patients with solid tumors during therapy or to identify individuals having a non detected tumor. Increase and decrease in the number of epithelial tumor cells in peripheral blood may serve as a marker for timely and closely monitoring the response to a tumor therapy. An increasing number of epithelial tumor cells in peripheral blood may indicate resistance of a fraction of the cells to chemotherapy and/or increasing growth potential of the tumor cells.

DESCRIPTION OF THE DRAWING

The FIGURE shows the recovery of epithelial antigen-positive cells from blood using magnetic bead enrichment in dependency on the concentration of these cells in blood.

DETAILED DESCRIPTION

Figure 1:
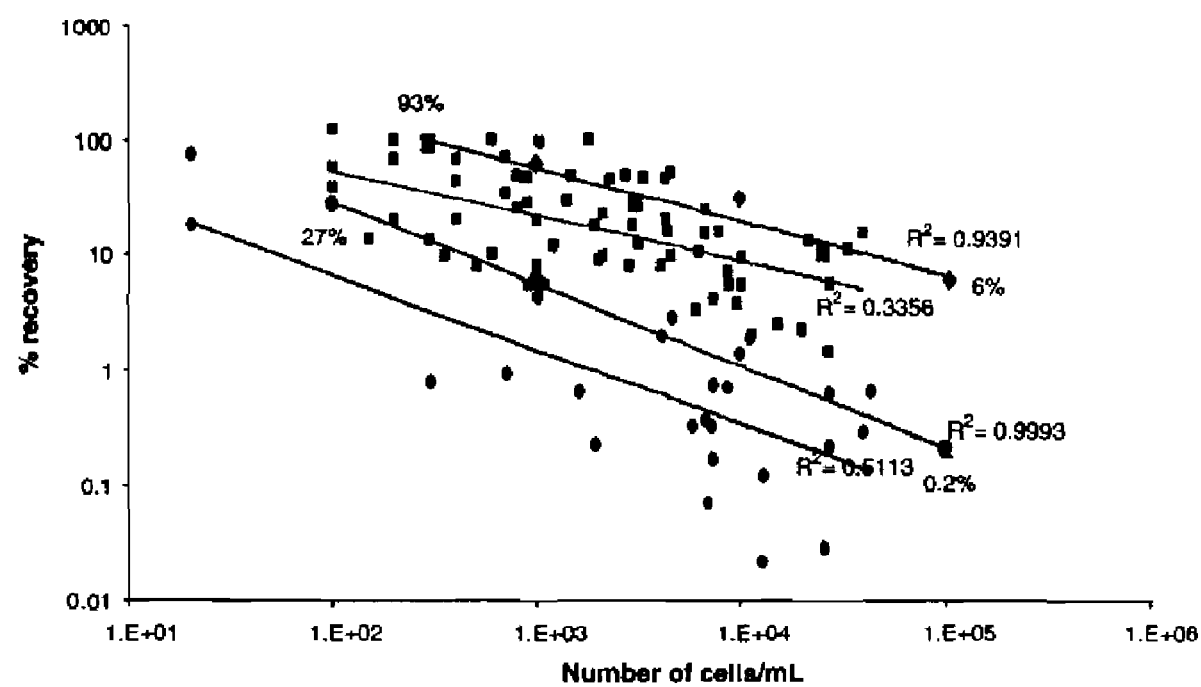

The invention establishes a method for determining the concentration of vital epithelial tumor cells in a body fluid. Epithelial tumor cells in a test specimen of the body fluid are fluorescence labeled. The test specimen is applied to a first support and incubated on said first support to let the epithelial tumor cells adhere to said first support. Adhering vital epithelial tumor cells are identified and quantified. Prior to applying the test specimen to the first support no enrichment of the epithelial tumor cells by means of binding to paramagnetic or magnetic particles and applying a magnetic force to the particles is performed.

The inventors have recognized that enrichment of the epithelial tumor cells by means of binding to paramagnetic or magnetic particles and applying a magnetic force to the particles always results in a loss or damage of epithelial tumor cells. The loss or damage depends on the particles, the incubation time of the epithelial tumor cells with the particles, the total concentration of cells in the body fluid and other factors. Therefore, a standardized quantification of vital epithelial tumor cells shall not comprise any enrichment of epithelial tumor cells by means of binding to paramagnetic or magnetic particles and applying a magnetic force to the particles. When applying the test specimen to the first support and incubating the test specimen on that first support 100% or nearly 100% of the vital epithelial tumor cells in the test specimen adhere to said first support. Furthermore, the inventors recognized that the number of vital epithelial tumor cells in the body fluid of patients having an epithelial tumor up to now was underestimated. The number proved to be sufficient for a direct quantification without any enrichment step before the adhesion of the vital tumor cells to the first support.

The method according to the invention is more reliable and faster to perform than the methods known from the state of the art. When recognizing that the enrichment step performed according to the state was not necessary the inventors overcame a technical prejudice. Formerly it was thought that an enrichment step is necessary to provide enough cells to be able to quantify the cells with an optical method.

According to a preferred embodiment no enrichment of the epithelial tumor cells by means of binding to a second support is performed. The second support may be an affinity column or a particle or a surface with a specific affinity for epithelial cells. It is further preferred when no enrichment of the epithelial tumor cells by means of specific binding to immobilized first antibodies or fragments of the first antibodies or to immobilized second antibodies or fragments of second antibodies is performed. The first antibodies or fragments of the first antibodies or the second antibodies or fragments of second antibodies may be immobilized on the paramagnetic or magnetic particles or on the second support. If immobilized antibodies are used a number of epithelial tumor cells is not bound by the immobilized antibodies and therefore escapes detection.

According to a further preferred embodiment of the present invention no washing step is performed. By performing a washing step a further loss of epithelial tumor cells may occur. However, since the vital epithelial tumor cells can be distinguished from other cells by their morphology and by the bound fluorescence labeled first antibodies or fragments of first antibodies it is not necessary to wash away other cells.

It is preferred when the first antibodies or the fragments of the first antibodies specifically bind to epithelial cells that are of human origin. According to a preferred embodiment of the invention the first antibodies or fragments of the first antibodies are directed against human epithelial antigen, wherein that human epithelial antigen is an antigen that is recognized by the monoclonal antibody HEA 125. This antibody is described, e.g. in Simon, B. et al., Proc. Natl. Acad. Sci. USA, Vol. 87, pp. 2755 to 2759, April 1990, Cell Biology.

It is preferred when the first support consists of a material that supports a non-specific adhesion of cells or that is coated with a substance supporting a non-specific adhesion of cells. For example, the first support may be an adhesion slide (Menzel GmbH & Co. KG, Braunschweig, Germany). This is a glass slide with special surface properties supporting a non-specific adhesion of cells. In this case also dead epithelial tumor cells adhere to the support. However, vital epithelial tumor cells can be distinguished from dead epithelial tumor cells by their morphology. The substance supporting the non-specific adhesion of cells may be poly-L-lysin. This measure rises the probability of identifying 100% of vital epithelial tumor cells contained in the test specimen. According to a preferred embodiment of the invention the morphology of the adhering epithelial tumor cells is analyzed by means of laser scanning cytometry or a computer-assisted image recognition method.

Laser scanning cytometry allows analysis of up to 50,000 cells in half an hour. Furthermore, laser scanning cytometry allows a relocation and reanalysis of defined cells that helps to further clarify the nature of these cells. Laser scanning cytometry further allows to reliably detect living tumor cells due to exclusive surface staining, to omit dead cells, which also show intracellular staining, and to discriminate between unspecific fluorescence events and true cells.

The laser scanning cytometry may also be used to determine the maximum fluorescence intensity and/or the total fluorescence per cell. Background fluorescence may be determined dynamically. This means that background fluorescence is determined for each single cell in the area immediately neighboring the cell. Background fluorescence is the fluorescence of the cell that is not caused by the fluorochrome. The value determined in this way is subtracted from the total fluorescence determined for each cell. In this way for each cell comparable fluorescence values are determined. Background fluorescence may be determined by laser scanning cytometry.

The body fluid may be blood, preferably peripheral blood, bone marrow, bone marrow aspirate, transudate, exudate, lymph, apheresis fluid, ascites, urine, saliva, and drainage fluids from wound secretions. If the body fluid is blood erythrocytes contained in the test specimen are preferably separated from the test specimen because they are present in an amount that may influence the optical determination of the morphology of the vital epithelial tumor cells. The separation of the erythrocytes from the test specimen may be performed by the following method:

The erythrocytes are lyzed and afterwards the test specimen is centrifuged to produce a pellet and a supernatant. The supernatant is discarded prior to suspending the pellet comprising the epithelial tumor cells and the labeling of the epithelial tumor cells. The suspended pellet is a preparation obtained from the test specimen in the sense of step b) of the method according to the invention. The erythrocytes may be lyzed by means of osmotic shock. This may be performed by mixing one part of peripheral blood with two parts of a buffer composed of 155 mmol/l $NH_4Cl$, 10 mmol/l $KHCO_3$, 1 mmol/l $Na_2$-EDTA.

A blocking reagent is advantageously added to the test specimen prior to the labeling of the epithelial tumor cells, wherein the blocking reagent blocks non-specific binding of the first antibodies or fragments of the first antibodies to the tumor cells. The blocking reagent may be a reagent that blocks the non-specific binding of the first antibodies or fragments of the first antibodies to Fc-receptors of the epithelial tumor cells.

In a further preferred embodiment the first antibodies directed against human epithelial antigen are from mice. Preferably, the fluorochrome is fluorescein isothiocyanate (FITC).

The invention will be further described in the following example, which does not limit the scope of the invention described in the claims:

EXAMPLE

Samples of peripheral blood were drawn from patients with lung or breast cancer and normal healthy donors. The blood of the healthy donors was spiked with cells of the breast cancer cell-line MCF-7 (ATCC No.: HTB-22). Peripheral blood leukocytes and tumor cell-line cells were counted in a Cell-Dyn 3200 (Abbott, Wiesbaden, Germany). Different numbers of between $10^5$ and 100 cell-line cells were each mixed with 1 ml of normal donor's whole blood containing $6 \times 10^6$ leukocytes.

For direct measurement without enrichment by means of binding to a second support 1 ml of the spiked blood or of the blood from the patients was subjected to red blood cell lysis using 10 ml of erythrocyte lysis solution (Qiagen, Hilden, Germany) for 10 min in the cold. The white cell pellet was then spun down at 700×g and re-diluted in 1 ml of PBS. 10 µl of fluorescein isothiocyanate (FITC)-conjugated mouse anti-human epithelial antibody (HEA, Miltenyi, Bergisch-Gladbach, Germany) were added to 100 µl of each cell suspension incubated for 15 min in the dark and readjusted to 1 ml. 100 µl of this suspension (corresponding to 10 µl of the original blood sample) were used for measurements.

For enrichment by means of binding to paramagnetic particles samples of the spiked blood and of the blood from patients with lung or breast cancer were used.

For the enrichment using paramagnetic HEA conjugated beads the cells were treated according to the manufacturer's instructions. In short, after erythrocyte lysis the white cell pellet from 1 to 10 ml of blood was resuspended in 400 µl of PBS and incubated with 30 µl of Fc-receptor blocking reagent (Miltenyi), 100 µl of HEA microbeads (Miltenyi) and 50 µl of FITC-conjugated mouse antihuman epithelial antibody (HEA-FITC-antibody, Miltenyi) for 30 min in the cold. A column provided by the manufacturer was attached to the magnet and washed according to the manufacturer's instructions. Afterwards the bead-coated cells were applied to the column. Non bound cells were then eluted by rinsing with 5×500 µl of buffer and the columns where removed from the magnet. The cells retained in the column were flushed out with 500 µl of additional buffer and were then used for measurements.

The enrichment using paramagnetic CellSelect beads (beads coated with an anti-epithelial cell antibody provided by Labsoft GmbH, Halle, Germany) was performed as follows: After erythrocyte lysis the white cell pellet of blood was diluted in 500 µl of PBS, 15 µl of paramagnetic beads and 15 µl of FITC-labeled HEA antibody. After incubation of the sample with careful overhead mixing for 15 min, the tube was attached to the magnet provided by the manufacturer and incubated for another 20 min in the cold with overhead mixing carried out four times. Cells carrying magnetic beads attached to the tube wall. The supernatant devoid of labeled cells was then carefully removed. The remnant cells containing fluorescence-labeled epithelial cells were diluted in 200 µl of buffer for subsequent measurements.

For measurements, cells from the previous preparations were applied to adhesion slides (Menzel GmbH & Co. KG, Braunschweig, Germany). 10 to 15 min after addition of 100 µl of cell suspension to the slides, living cells adhered to the surfaces of the slides. Measurements were started when the cells had settled. Optimal measurement required a single cell suspension with a space of approximately two to three cell diameters between the cells. Adherent cells were measured using a laser scanning cytometer (LSC; Compucyte Corporation, Cambridge, Mass., USA). Vital cells could easily and unequivocally be contoured using forward scatter as a threshold parameter at 20× magnification. A defined area covered with 100 µl of cell suspension was used for analysis. Background fluorescence was determined dynamically to calculate both peak and integral fluorescence on a per-cell basis. This method corrects for variations in background fluorescence, thus achieving equivalent fluorescence calculation for all cells. FITC-HEA positive cell fluorescence was collected using a 530/30-nm bandpass filter and a photomultiplier. This system is able to detect one positive cell among 100,000 negative events. Exclusive surface staining was taken as proof of cell viability.

Optical methods allow the reliable detection of one positive cell among 100,000 cells without enrichment by binding to a second support. 100,000 cells correspond to approximately 10 µl of whole blood. The number of cells retrieved with either the Miltenyi or the Labsoft procedure was compared for the addition of between $10^5$ and 100 MCF-7 cells to 1 ml of peripheral whole blood of normal donors.

The results are shown in the FIGURE. In case of samples spiked with tumor cells 100% is the number of cells added to a blood sample and in case of patient samples 100% is the number of cells detected without any enrichment step. The meaning of the symbols is as follows:

Big squares and diamonds: Recovery of epithelial cells using CellSelect beads (Labsoft, Halle, Germany) of cells of the cell line MCF-7 breast cancer cells in 1 ml of whole blood.

Big circles: Recovery of epithelial cells using HEA beads (Miltenyi, Bergisch-Gladbach, Germany) of whole blood spiked with MCF-7 breast cancer cells.

Small squares: Percentage of epithelial cells from 66 patient samples recovered with CellSelect beads as compared to numbers determined by red blood cell lysis without magnetic enrichment Small circles: Numbers of epithelial cells from 22 patient samples recovered with HEA beads as compared to numbers determined by red blood cell lysis without magnetic enrichment.

Regression lines: Least-squares regression.

With increasing numbers of MCF-7 cells admixed with whole blood, the recovery decreased. When using the blood samples of the tumor patients the percentage of the tumor cells that could be detected after magnetic enrichment decreased with increasing number of tumor cells as determined directly after red blood cell lysis without magnetic enrichment. The experiment shows that the biggest portion of the epithelial tumor cells contained in a test specimen can be detected by direct adhesion of the cells to a first support without any enrichment by means of binding to magnetic particles.

It is to be understood that while the invention has been described in conjunction with the detailed description thereof, the forgoing description is intended to illustrate and not limit the scope of the invention, which is defined by the scope of the appended claims. Other aspects, advantages, and modifications are within the scope of the following claims.

What is claimed is:

1. A method for determining the concentration of vital epithelial tumor cells in a body fluid, comprising the following steps:
    a) obtaining from the body fluid of a test subject a test specimen comprising a mixed cell population suspected of containing epithelial tumor cells, b) labeling the epithelial tumor cells by addition, to the test specimen or to a preparation obtained from the test specimen, of first antibodies or fragments of first antibodies that specifically bind to epithelial cells, which first antibodies or fragments of first antibodies are bound to a fluorochrome, wherein the first antibodies or fragments of first antibodies are directed against human epithelial antigen, wherein said human epithelial antigen is an antigen that is recognized by the monoclonal antibody HEA 125, c) applying the test specimen to a first support and incubating the test specimen on said first support to let the epithelial tumor cells in said test specimen adhere to said first support, and d) identifying and quantitating vital cells of the adhering epithelial tumor cells by means of their morphology and calculating the concentration of vital epithelial tumor cells in the body fluid, wherein the morphology of the adhering epithelial tumor cells is analyzed by means of laser scanning cytometry, wherein living tumor cells are detected due to exclusive surface staining and dead cells are omitted due to intracellular staining, wherein no enrichment of the epithelial tumor cells is performed before the adhesion of the epithelial tumor cells to said first support, wherein no washing step is performed.

2. A method for determining the concentration of vital epithelial tumor cells in a body fluid, comprising the following steps:

a) obtaining from the body fluid of a test subject a test specimen comprising a mixed cell population suspected of containing epithelial tumor cells, b) labeling the epithelial tumor cells by addition, to the test specimen or to a preparation obtained from the test specimen, of first antibodies or fragments of first antibodies that specifically bind to epithelial cells, which first antibodies or fragments of first antibodies are bound to a fluorochrome, wherein the first antibodies or fragments of first antibodies are directed against human epithelial antigen, wherein said human epithelial antigen is an antigen that is recognized by the monoclonal antibody HEA 125, c) applying the test specimen to a first support and incubating the test specimen on said first support to let the epithelial tumor cells in said test specimen adhere to said first support, and d) identifying and quantitating vital cells of the adhering epithelial tumor cells by means of their morphology and calculating the concentration of vital epithelial tumor cells in the body fluid, wherein the morphology of the adhering epithelial tumor cells is analyzed by means of laser scanning cytometry, wherein living tumor cells are detected due to exclusive surface staining and dead cells are omitted due to intracellular staining, wherein laser scanning cytometry is also used to determine the maximum fluorescence intensity and/or the total fluorescence per cell, wherein no enrichment of the epithelial tumor cells is performed before the adhesion of the epithelial tumor cells to said first support.

3. A method for determining the concentration of vital epithelial tumor cells in a body fluid, comprising the following steps:

a) obtaining from the body fluid of a test subject a test specimen comprising a mixed cell population suspected of containing epithelial tumor cells, b) labeling the epithelial tumor cells by addition, to the test specimen or to a preparation obtained from the test specimen, of first antibodies or fragments of first antibodies that specifically bind to epithelial cells, which first antibodies or fragments of first antibodies are bound to a fluorochrome, wherein the first antibodies or fragments of first antibodies are directed against human epithelial antigen, wherein said human epithelial antigen is an antigen that is recognized by the monoclonal antibody HEA 125, c) applying the test specimen to a first support and incubating the test specimen on said first support to let the epithelial tumor cells in said test specimen adhere to said first support, and d) identifying and quantitating vital cells of the adhering epithelial tumor cells by means of their morphology and calculating the concentration of vital epithelial tumor cells in the body fluid, wherein the morphology of the adhering epithelial tumor cells is analyzed by means of laser scanning cytometry, wherein living tumor cells are detected due to exclusive surface staining and dead cells are omitted due to intracellular staining, wherein background fluorescence is dynamically determined, wherein no enrichment of the epithelial tumor cells is performed before the adhesion of the epithelial tumor cells to said first support.

4. A method for determining the concentration of vital epithelial tumor cells in a body fluid, comprising the following steps:

a) obtaining from the body fluid of a test subject a test specimen comprising a mixed cell population suspected of containing epithelial tumor cells, wherein the body fluid is blood and erythrocytes contained in the test specimen are separated from the test specimen, b) labeling the epithelial tumor cells by addition, to the test specimen or to a preparation obtained from the test specimen, of first antibodies or fragments of first antibodies that specifically bind to epithelial cells, which first antibodies or fragments of first antibodies are bound to a fluorochrome, wherein the first antibodies or fragments of first antibodies are directed against human epithelial antigen, wherein said human epithelial antigen is an antigen that is recognized by the monoclonal antibody HEA 125, c) applying the test specimen to a first support and incubating the test specimen on said first support to let the epithelial tumor cells in said test specimen adhere to said first support, and d) identifying and quantitating vital cells of the adhering epithelial tumor cells by means of their morphology and calculating the concentration of vital epithelial tumor cells in the body fluid, wherein the morphology of the adhering epithelial tumor cells is analyzed by means of laser scanning cytometry, wherein living tumor cells are detected due to exclusive surface staining and dead cells are omitted due to intracellular staining, wherein no enrichment of the epithelial tumor cells is performed before the adhesion of the epithelial tumor cells to said first support.

5. The method according to claim 4, wherein the erythrocytes are lyzed and afterwards the test specimen is centrifuged to produce a pellet and a supernatant, and wherein the supernatant is discarded prior to suspending the pellet comprising the epithelial tumor cells and the labeling of the epithelial tumor cells.

6. The method according to claim 5, wherein the erythrocytes are lyzed by means of osmotic shock.

7. The method according to claim 1, 2, 3, or 4, wherein no enrichment of the epithelial tumor cells by means of binding to a second support is performed.

8. The method according to claim 1, 2, 3, or 4, wherein no enrichment of the epithelial tumor cells by means of specific binding to immobilized first antibodies or fragments of the first antibodies or to immobilized second antibodies or fragments of second antibodies is performed.

9. The method according to claim 1, 2, 3, or 4, wherein the first support consists of a material that supports a nonspecific adhesion of cells or that is coated with a substance supporting a nonspecific adhesion of cells.

10. The method of claim 9, wherein the substance is poly-L-lysin.

11. The method according to claim 1, 2, 3, or 4, wherein the body fluid is selected from the group consisting of blood, bone marrow, bone marrow aspirate, transudate, exudate, lymph, apheresis fluid, ascites, urine, saliva, and drainage fluids from wound secretions.

12. The method according to claim 1, 2, 3, or 4, further comprising adding a blocking reagent to the test specimen prior to the labeling of the epithelial tumor cells, wherein the blocking reagent blocks non-specific binding of the first antibodies or fragments of first antibodies to the tumor cells.

13. The method according to claim 12, wherein the blocking reagent is a reagent that blocks the non-specific binding of the first antibodies or fragments of the first antibodies to Fc-receptors of the epithelial tumor cells.

14. The method according to claim 1, 2, 3, or 4, wherein the first antibodies directed against human epithelial antigen are from mice.

15. The method according to claim 1, 2, 3, or 4, wherein the fluorochrome is fluorescein isothiocyanate (FITC).

* * * * *